United States Patent [19]

DiBiasio et al.

[11] 3,958,013

[45] May 18, 1976

[54] HALOGENATED CYCLOBUTYL ETHER ANESTHETICS

[75] Inventors: Vincent I. DiBiasio, Billerica; Charles W. Simons, Bedford; Gerald J. O'Neill, Arlington, all of Mass.

[73] Assignee: W. R. Grace & Co., Cambridge, Mass.

[22] Filed: Jan. 10, 1975

[21] Appl. No.: 540,075

[52] U.S. Cl. .................................. 424/339
[51] Int. Cl.$^2$ ................................ A61K 31/075
[58] Field of Search ........................ 424/339

[56] References Cited
UNITED STATES PATENTS 3,870,797   3/1975   Holdswouth et al. .......... 424/352

*Primary Examiner*—Jerome D. Goldberg
*Attorney, Agent, or Firm*—Armand McMillan; C. E. Parker

[57] ABSTRACT

The following halogenated cyclobutyl ethers have been found to possess utility as general anesthetics: 1-chloro-2-methoxy-1,2,3,3,4,4-hexafluorocyclobutane, 1-chloro-2-methoxy-1,4,4-trifluorocyclobutane and 1-bromo-2-methoxy-1,2,3,3,4,4-hexafluorocyclobutane.

4 Claims, No Drawings

HALOGENATED CYCLOBUTYL ETHER ANESTHETICS

THE PRIOR ART

Due in part to the unpredictable chemical and physiological properties and behavior of organic compounds, such as for instance the halogenated alkanes, and to the lack of understanding of the mode of action of anesthetics in general, the search for useful new inesthetic agents remains beyond the scope of the routine expertise of both the chemist and the physiologist. Thus it is, for instance, that while cyclopropane is an effective if inflammable anesthetic one of its neighboring water-insoluble homologs, cyclopentane, has no medical utility. As to cyclobutanes, a recent review of the state of the art [Larsen, E. R., Fluorine Chemistry Reviews, Vol. 3, page 1 and 34 (1969)] is no more enlightening in its report that of three closely related fluorocyclobutanes, one possesses anesthetic properties (1,2-dihydrohexafluoro-) while its more highly halogenated homologs are toxic (1,2-dichlorohexafluoro-) and inactive (octafluoro-). Further developments in the synthesis and testing of halogenated cyclobutyl ethers have also failed to provide any reliable guidelines for the discovery of unknown structures of utility in the anesthetic art.

SUMMARY OF THE INVENTION

It has now been discovered that the following cyclobutyl ethers possess utility as general inhalation anesthetics: 1-chloro-2-methoxy-1,2,3,3,4,4-hexafluorocyclobutane, 1-chloro-2methoxy-1,4,4-trifluorocyclobutane, and 1-bromo-2-methoxy-1,2,3,3,4,4-hexafluorocyclobutane.

DETAILED DESCRIPTION

The compounds of this invention can be prepared by cyclizing appropriately selected ethylenic compounds in the presence of certain polymerization inhibitors. The cyclization method has been generally described by Coffman et al. [J. Am. Chem. Soc, 71, 490 (1949)].

The ethylenic compounds are typically charged into an autoclave with such inhibitors as phenothiazine, β-pinene and the like, and the mixture is heated at a suitable temperature, e.g. at 150°C for 12 hours, under autogenous pressure. When the reaction is complete, the autoclave is cooled and gaseous substances are evacuated through a cold trap. The liquid contents are then removed and subjected to a preliminary distillation followed by final purification by means of preparatory scale vapor phase chromatography or by other suitable techniques. Compounds of sufficiently high purity for anesthetic use are obtained in this manner.

Some of the ethlenic compounds that may be employed to synthesize the anesthetic products of the invention are listed in Table I along with some of the physical properties of the products. It should be noted that the cyclobutyl ethers used in this invention may also be obtained from different pairs of ethylenic compounds, with or without further post-cyclization halogenation. For instance, the ether of Example I may be synthesized by the cyclization of β-chlorodifluorovinylmethyl ether with tetrafluoroethylene.

Table 1

Synthesis and Physical Properties of Anesthetic Compounds

| Ex. | Cyclobutane | Reactants | Density | Boiling Point |
|---|---|---|---|---|
| 1 | 1-Cl-2-methoxy-hexafluoro- | $F_2C=CF-O-CH_3$ $+F_2C=CFCl$ | $1.521^{27.5}$ | 89°C |
| 2 | 1-Cl-2-methoxy-1,4,4-trifluoro- | $H_2C=CH-O-CH_3$ $+F_2C=CFCl$ | $1.323^{24}$ | 120.8° |
| 3 | 1-Br-2-methoxy hexafluoro- | $F_2C=CF-O-CH_3$ $+F_2C=CFBr$ | $1.780^{25}$ | 104° |

The cyclobutyl ethers shown in Table 1 are clear liquids at room temperature. They can be stored in containers of the type commonly used for conventional anesthetics of comparable boiling point, e.g. halothane.

ANESTHETIC PROPERTIES

The physiological effects of the cyclobutyl ethers of this invention were demonstrated upon mice using a standard test for evaluation of inhalation anesthetics, similar to that described by Robbins [Pharmacoloy and Experimental Therapeutics 86, 197 (1946)]. In this test, mice were exposed to the compound for a period of 10 minutes in a rotating drum. Observations were made of the pinch reflex, the corneal reflex and the return of the righting reflex. At least four graded doses were employed to determine the minimum concentration required to anesthetized 50% of the mice ($AC_{50}$) and the minimum concentration required to kill 50% of the mice ($LC_{50}$). The anesthetic index (AI) was then calculated from these minimum concentrations. The data obtained with the compounds of Example 1 to 4 are presented in Table 2.

Table 2

| Ex. | Cyclobutane | Anesthetic Data $AC_{50}$ | $LC_{50}$ (% volume) | AI |
|---|---|---|---|---|
| 1 | 1-Cl-2-MeO-hexafluoro- | 2–4%* | 7–8% | ~2 |
| 2 | 1-Cl-2-MeO-1,4triF- | <1% | >2% | >2 |
| 3 | 1-Br-2-MeO-hexafluoro- | <1% | >2.5% | >2.5 |

*When two values are given, the actual value lies between them.

The compounds of this invention are therefore capable of inducing a state of anesthesia in air-breathing mammals, from which the latter recover, provided that the lethal concentration of anesthetic vapors is not reached. It is contemplated the ethers just disclosed may be used in admixtures with pharmaceutically acceptable diluents and stabilizers such as thymol, or in combination with one or more of the known inhalation anesthetics, such as nitrous oxide, ether, halothane, chloroform, methoxyflurane, and the like.

What is claimed is:

1. The process of inducing anesthesia in a mammal, which comprises administering by inhalation to said mammal an effective quantity for inducing anesthesia of a 2-methoxy-cyclobutyl ether selected from the group consisting of: 1-chloro-2-methyoxy-1,2,3,3,4,4-hexafluorocyclobutane, 1-chloro-2-methoxy-1,4,4-trifluorocyclobutane and 1-bromo-2-methoxy-1,2,3,3,4,4-hexaflurocyclobutane.

2. The process of claim 1 wherein the ether administered is 1-chloro-2-methoxy-1,2,3,3,4,4-hexafluorocyclobutane.

3. The process of claim 1 wherein the ether administered is 1-chloro-2-methoxy-1,4,4-trifluorocyclobutane.

4. The process of claim 1 wherein the ether administered is 1-bromo-2-methoxy-1,2,3,3,4,4-hexafluorocyclobutane.

* * * * *